United States Patent [19]

Herrin

[11] Patent Number: 4,773,857
[45] Date of Patent: Sep. 27, 1988

[54] METHOD AND APPARATUS FOR SECURING A RUBBER DAM

[75] Inventor: Hermon K. Herrin, Harris, Tex.

[73] Assignee: Board of Regents, The University of Texas System, Austin, Tex.

[21] Appl. No.: 57,320

[22] Filed: Jun. 4, 1987

[51] Int. Cl.⁴ .............................................. A61C 5/12
[52] U.S. Cl. ...................................... 433/138; 433/9; 433/180
[58] Field of Search .................. 433/9, 136, 138, 139, 433/180

[56] References Cited

U.S. PATENT DOCUMENTS

| | | |
|---|---|---|
| 138,370 | 4/1873 | Blake . |
| 1,321,451 | 11/1919 | Ivory . |
| 1,520,753 | 12/1924 | Ivory . |
| 1,550,425 | 8/1925 | Burlew . |
| 1,970,875 | 8/1934 | Andaloro . |
| 2,632,533 | 3/1953 | MacKenzie ........................ 446/122 |
| 2,680,908 | 6/1954 | Daigle . |
| 2,835,628 | 5/1958 | Saffir . |
| 3,421,222 | 1/1969 | Newman . |
| 3,491,447 | 1/1970 | Newman . |
| 4,179,815 | 12/1979 | Hoffman . |
| 4,204,329 | 5/1980 | Kahn . |
| 4,433,960 | 2/1984 | Garito et al. . |
| 4,514,174 | 4/1985 | Dougherty et al. . |
| 4,608,021 | 8/1986 | Barrett . |
| 4,661,063 | 4/1987 | Levy ................................... 433/139 |

FOREIGN PATENT DOCUMENTS 828287 7/1949 Fed. Rep. of Germany .
61470 1/1979 Sweden .

OTHER PUBLICATIONS

Leon Ireland, *The Rubber Dam, Its Advantages and Application* Mar., 1962, Texas Dental Journal, pp. 8, 9, 10.

Primary Examiner—Carroll B. Dority, Jr.
Attorney, Agent, or Firm—Arnold, White & Durkee

[57] ABSTRACT

A compact dam clamp and its method of application is disclosed, said dam clamp having in a preferred embodiment a side attachment face and a bottom face, said side attachment face being provided with one or more apertures provided therethrough to enable the clamp to be physically locked to the tooth upon application and curing of a non permanent composite resin. The use of the present device does not result in either hard or soft tissue damage, and may be used on even partially erupted teeth.

27 Claims, 2 Drawing Sheets

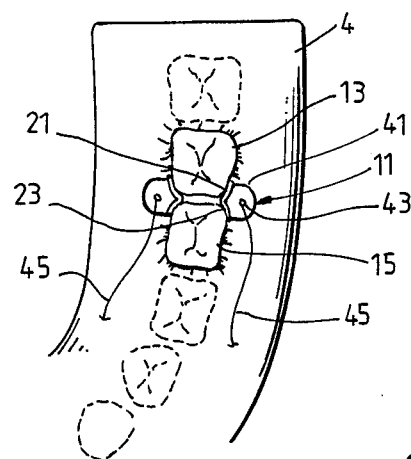
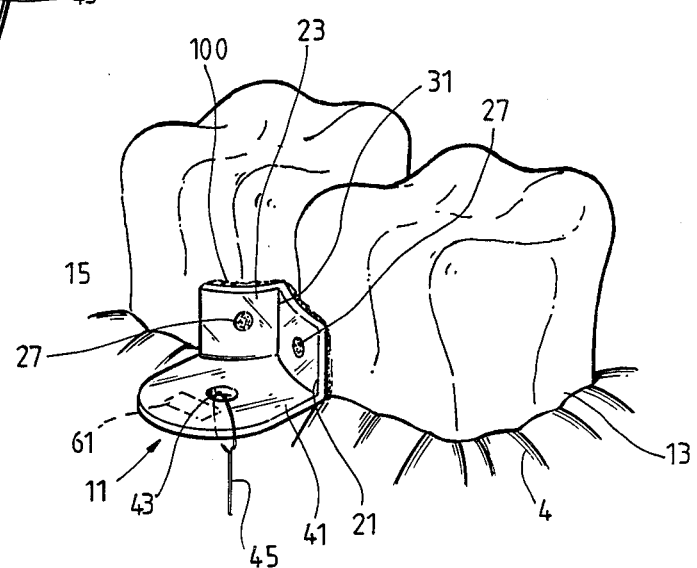
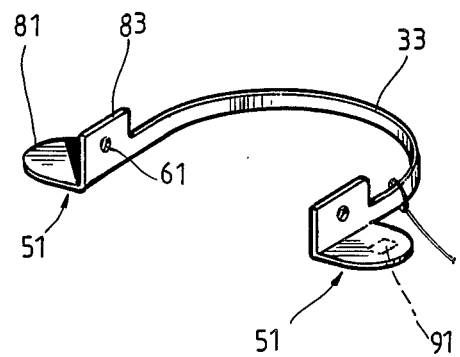

METHOD AND APPARATUS FOR SECURING A RUBBER DAM

BACKGROUND OF THE INVENTION

1. Field of the Invention

This invention relates generally to a clamp to be used to secure a rubber dam over one or more teeth during restorative dental procedures or the like and to a method of using said clamp. More particularly, the present invention relates to a compact dam clamp which is designed to isolate a dental work area within the mouth without causing hard or soft tissue damage to the tooth or the surrounding gum area.

2. Background

Restorative dental procedures often require that one or more teeth be isolated from moisture contamination caused by the tongue or other moist surfaces of the mouth. Additionally, restorative and similar procedures often necessitate a work area within the mouth which is sealed off from the upper throat area so that filling compounds or other incidental particulates cannot be inadvertently aspirated or swallowed.

In most cases where this type of control is needed, a rubber "dam" is placed over and around one or more teeth to prevent moisture from entering the work area, and to act as a physical barrier to prevent the downward migration of unwanted particles. These rubber dams usually consist of a small rectangular rubber sheet which is provided with appropriately sized apertures throughout so as to allow the placement of the dam over and around a tooth or group of teeth. However, a common problem associated with the use of such a system is the maintenance of the dam in place over and around these teeth while a given dental procedure is being performed.

Various attempts have been made toward the design of a mechanism which could control a rubber dam from slipping up and off the tooth during an ongoing dental procedure. One such device designed to meet this need is seen in U.S. Pat. No. 1,321,451. The metal dam clamps disclosed in that patent are generally characterized by two horizontally opposed and serrated surfaces which are connected by a resilient brace. Spring tension derived from the brace compressively closes and holds these grip surfaces on the tooth, thus securing the position of a given rubber dam.

Such resilient metal clamps, however, have many disadvantages. One such disadvantage is the overall bulk of the system. In the usual case during restorative or similar procedures, operating space within the oral cavity is limited due to the presence of a variety of dental instruments as well as limitations in the jaw opening itself. Therefore, any tool or instrument involved in such a procedure must necessarily be compact in size so it will not hinder the view of the tooth or impede the movement of instruments there about. Additionally, the very nature of the resilient clamp makes it prone to cause both hard and soft tissue damage, as well as causing damage to existing restorations. Clamps of this type are also almost useless when the tooth is only partially erupted. Finally, clamps of this design are radiographically opaque which usually necessitates their removal before a given x-ray series is undertaken.

SUMMARY OF THE INVENTION

The present invention overcomes many of the disadvantages of prior art clamps by providing an effective yet compact dam clamp which may be used on teeth in all stages of maturity and whose use will not precipitate either hard or soft tissue damage.

In a preferred embodiment of the present invention, a plastic L-shaped device or clamp is formed with both a bottom face and a side attachment face. The side attachment face of the device is preferably arcuate in shape so as to fit the external contour of a given tooth. In preferred embodiments, this side face may be provided with one or more apertures so that the clamp may be affixed to the tooth enamel by a composite resin material applied thereto. These apertures are preferably configured in the shape of a truncated cone, with the smaller diameter opening of the aperture terminating on the attachment face of the clamp. Apertures configured in such a fashion are better able to lock the side attachment face to the tooth enamel upon application and curing of a suitable composite resin.

The bottom face of the device or clamp is generally planar in configuration and some embodiments may contain one or more apertures to allow for attachment of ligation material or other filament to insure the clamp will not be inadvertently aspirated during placement of the clamp on a given tooth. It is envisioned that a radiographically opaque tab may be disposed in the bottom face of the tab to aid in its location and retrieval should the clamp be inadvertently aspirated or swallowed.

The use of the present device may be described as follows. After placement of the rubber dam over the subject tooth, the dam is held in place manually while a small area of enamel is chemically etched for 10-15 seconds on the buccal and lingual surfaces of the tooth and the apical one-third of the clinical crown. After the acid solution is rinsed, a small amount of composite material is placed on the clamp, insuring that the material penetrates the locking apertures. The clamp is then placed against the tooth and visible light is applied for ten seconds to cure the material.

Alternatively, the clamp may be secured to the tooth in the manner previously described before the rubber dam is placed over and about a given tooth. This later method may have particular utility in teeth which are only partially erupted.

In dental procedures involving anterior teeth, a modified version of the invention may be desired. Accordingly, in another embodiment of the device the side attachment faces of two L-shaped members may be coupled with a loop of plastic or other resilient material. In attachment to the tooth, this loop is positioned around the distal portion of the tooth and thus secures the backmost portion of the dam. The L-shaped members are attached on opposite sides of the tooth in a manner similar to that previously described. Utilizing such a setup, a given dam may be better secured over and around a rear tooth by the additional retaining surfaces provided thereby.

In yet another embodiment of the invention, a pair of attachment faces may be joined together in an L-shaped configuration, said configuration itself joined on one edge to a substantially planar base. Similar to other embodiments of the invention, one or both of the attachment faces may be provided with one or more apertures to enhance their ability to adhere and lock to a given tooth. This embodiment is secured in place in the interproximal area between two teeth in a manner similar to that previously described, and may have particular utility in applictions where work is to be performed on the labial or buccal surface of a given tooth.

It is envisioned that the present invention will preferably be formed out of a clear rigid plastic in order to best facilitate its attachment to a given tooth. The transparent or translucent qualities of the material is important in order to use a light cured resin composite material (bis-GMA) to lightly bond the clamp to the enamel of the tooth.

The present invention has many advantages over the prior art. First, the present invention offers a compact means for maintaining a rubber dam over and around one or more teeth during a given dental procedure. The compact nature of the device is important due to the limited work area available within the mouth as caused by the presence of other dental instruments as well as the limited size of the jaw opening itself.

Yet another advantage of the present invention is its ability to securely hold a rubber dam in place without causing either hard or soft tissue damage and further, without causing damage to existing restorations.

Another advantage of the present invention is the ability of the device to be used with only partially erupted teeth.

Yet another advantage of the present device is its ability to remain in the mouth while a given x-ray series is taken.

BRIEF DESCRIPTION OF THE DRAWINGS

The invention may be better understood by reference to the drawings listed below.

FIG. 4 illustrates a top view of a second embodiment of the present invention as it would be positioned in the mouth during a given dental procedure.

FIG. 5 illustrates a perspective view of the second embodiment of the present invention as it would be attached in the interproximal space between a pair of teeth.

FIG. 6 illustrates a perspective view of a third embodiment of the present invention.

DETAILED DESCRIPTION OF THE PREFERRED EMBODIMENT

Figure 1:
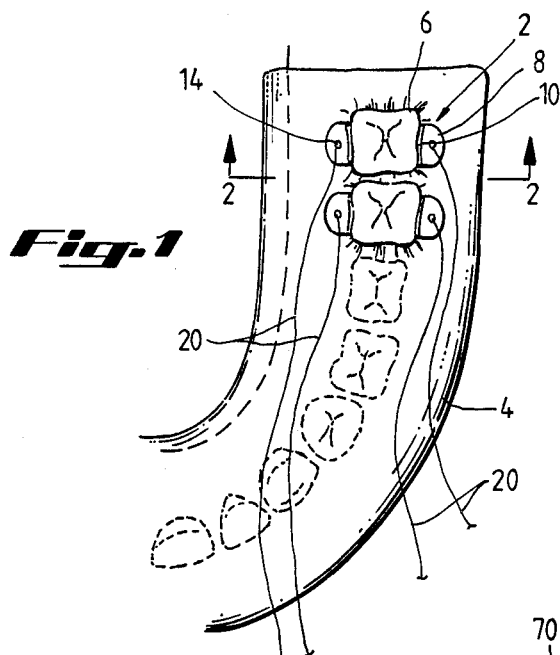
FIG. 1 generally illustrates a top view of the present invention as it would be positioned in the mouth during a given dental procedure.

FIG. 1 illustrates a top view of a device 2 of the present invention as it would be used in the mouth to secure a rubber dam 4 over and around a subject tooth 6.

Figure 2A:
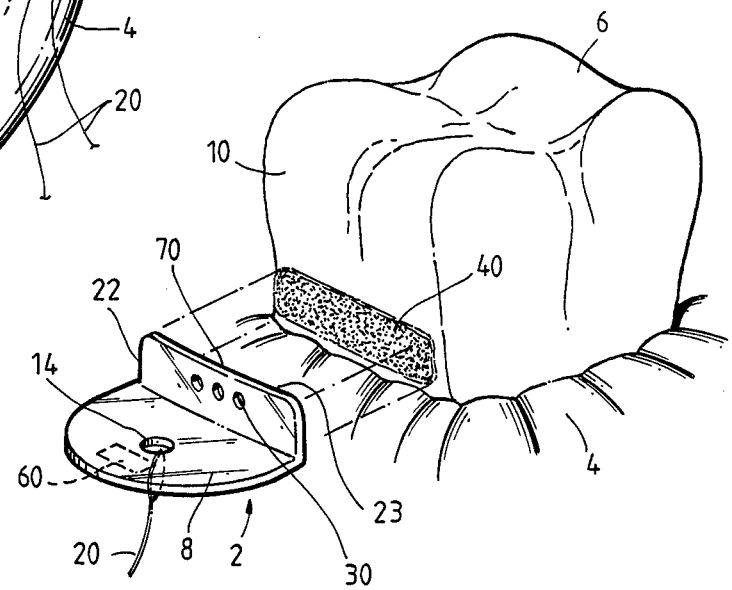
FIGS. 2A and 2B illustrate a perspective view of the invention as it would be attached to the labial or buccal surface of a given tooth.
Figure 2B:
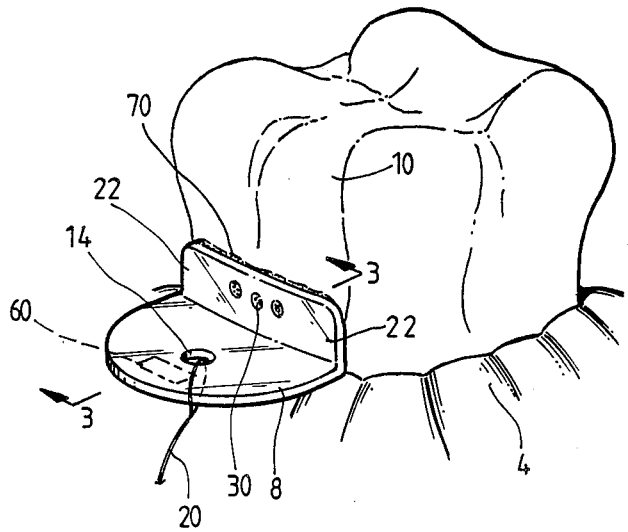
Figure 3:
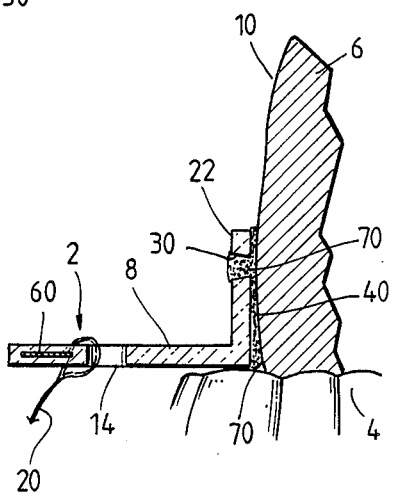
FIG. 3 illustrates a side view of the invention taken along plane 3—3 in FIG. 2B.

The apparatus shown in FIGS. 1–3 consists of the bottom face 8 of the clamp 2 as it would be situated relative to the side face 10 of a tooth 6. Also seen is an aperture 14 which is formed in the bottom face 8 of the clamp 2 such that ligation material 20 or the like may be secured to the clamp 2 to prevent accidental ingestion or aspiration.

FIGS. 2A and 2B illustrate perspective views of the preferred embodiment of the invention in relation to a given tooth 6, and may further serve to illustrate the method by which the present device may be utilized in the mouth to secure a rubber dam 4.

As shown in FIG. 2A, the invention consists of a side face 22 and a bottom face 8. Locking apertures 30 may be disposed in the side face 22 to aid in binding to the fixing surface 10 of the tooth 6. As noted in FIGURE 1, one or more apertures 14 may be provided in the bottom face 8 to attach ligation material 20 or the like to the clamp. A radiographically opaque tab 60 may also be provided in the bottom face 8 to aid in detection of the clamp should it be accidentally swallowed or aspirated.

Prior to bonding the clamp 2, a rubber dam 4 is placed over the tooth 6 by apertures specially provided in the rubber dam. These apertures are preferably smaller than the actual diameter of the tooth, such that a snug, resilient fit around the tooth is achieved.

When the dam 4 is in place over the tooth 6, a selected area of the attachment face 10 of the tooth 6 is treated with an acid solution and then rinsed. This treatment produces a special attachment site 40 on which the clamp 2 may be affixed by way of a non-permanent composite resin 70 applied to the contact surface 23 of the side face 22. Preferably, this resin material 70 is applied such that some of the material 70 extrudes through the back portions of the apertures 30 in the side face 22, so that a physical "lock" is achieved between the resin and the clamp. When a bond is made between the clamp 2 and the tooth 6, this composite resin is light cured.

FIG. 3 illustrates a side view of the invention taken through plane 3—3 of FIG. 2B. In this view may be seen the bottom face 8 and the side face 22 in relationship to the dam 4 and the tooth 6. Also in this illustration may be seen the relationship of the radiographic tab 60 to the ligation aperture 14. Of particular note in this view is the generally conical shape of the aperture 30 disposed through the side face 22. As may be seen, this aperture 30 is formed such that its smaller diameter terminates at the attachment surface 40 of the tooth 6, thus effectively locking the clamp 2 to the tooth upon curing of the resin 70.

FIGS. 4 and 5 illustrate a second embodiment of the present invention as it may be applied in the interproximal space between two teeth 13 and 15 so as to secure a dam 4. As may be seen by reference to FIG. 5, the clamp of this embodiment consists of two side attachment faces 21 and 23 which are joined together along a common edge 31 and whose relative size and angulation may differ commensurate with the given application for which the clamp is to be used. One or more locking apertures 27 may be provided in each face as an aid in bonding the clamp and as earlier described. Preferably, these apertures 27 are conical in configuration, with the larger diameter end of the aperture 27 terminating on the contact face 100 proximate teeth 13 and 15. These side attachment faces 21 and 23 are together secured to a bottom face 41. Preferably, disposed in this bottom face 41 is an aperture 43 designed to secure ligation material 45 or the like so as to prevent accidental aspiration or ingestion. A radiographically opaque tab 61 may also be provided in this bottom face.

FIG. 6 illustrates yet a third embodiment of the invention as it may be secured around an posterior tooth. In this view, two L-shaped members 51 are attached at the terminal ends of a loop 33 so as to fit around a back portion of a tooth and secure a rubber dam (not shown). Each L-shaped member 51 is provided with a bottom face 81 and a side attachment face 83. As in previous embodiments, each side attachment face 83 preferably defines one or more apertures 61 so as to aid in bonding the clamp 51 to the tooth. Likewise, each bottom face 81 is preferably provided with one or more apertures 91 so as to aid in securing ligation material or the like to the clamp.

What is claimed is:

1. A dental dam clamp comprising:
   an L-shaped plastic member having a generally planar bottom face and a side face, said side face provided with an aperture disposed therethrough to aid in bonding the ide face to a tooth via a bonding compound.

2. The dam clamp of claim 1 where the aperture disposed in the side face of the clamp is generally conical in configuration, with the smaller diameter end of the aperture terminating at the surface of the tooth.

3. The dam clamp of claim 1 where one or both faces of the clamp are composed of material which is substantially transparent or translucent to visible light.

4. The dam clamp of claim 1 where the bottom face is provided with an aperture extending therethrough so as to provide an attachment point for ligation material.

5. The dam clamp of claim 1 where the bottom face is provided with a radiographically opaque identification tab.

6. A dam clamp comprising:
   a clear plastic member having a bottom face and a side face;
   said bottom face being substantially planar and provided with one or more apertures disposed therethrough to allow the attachment of ligation material or the like; and
   said side face being generally arcuate in shape and being further provided with one or more apertures disposed therethrough to provide a means for bonding said side face to a tooth exterior via a bonding compound.

7. The dam clamp of claim 6 where the bottom face is provided with a radiographic identification tab disposed therein.

8. A dam clamp comprising:
   an L-shaped member having a bottom face and a side face, said bottom face being substantially planar in configuration, said side face adapted to attach a single contact surface of a given tooth via a bonding compound.

9. The dam clamp of claim 8 where the side face is provided with an aperture disposed therethrough so as to enhance the affixation of the side face to an exterior face of a tooth.

10. The dam clamp of claim 9 where the aperture disposed in the side face is substantially conical in configuration, with the end of the aperture having the smaller diameter being situated on the tooth contacting surface of said side face.

11. The dam clamp 8 where one or both faces of the clamp are composed of a material which is transparent or translucent to visible light.

12. The dam clamp of claim 8 where the bottom face is provided with one or more apertures disposed therethrough so as to provide an attachment point for ligation material.

13. The dam clamp of claim 8 where the bottom face is provided with a radiographically opaque identification tab.

14. A method for securing a rubber dam over and around a tooth using a dam clamp comprised of a L-shaped member having a bottom face and a side face, the method comprising:
   placing a rubber dam over and around a tooth such that a secure elastic fit is achieved;
   chemically etching the enamel of the tooth such as to produce an attachment site;
   affixing the clamp to the tooth utilizing a non permanent composite resin;
   curing said resin in situ by use of visible light.

15. A dam clamp comprising:
   an L-shaped member having a side face and a bottom face, said clamp adapted to be bonded to a tooth via a bonding compound.

16. The dam clamp of claim 15 further comprising an aperture disposed in said side face to aid in bonding the clamp to a tooth.

17. The dam clamp of claim 16 wherein said aperture is conical in configuration.

18. The dam clamp of claim 15 further comprising an aperture disposed in said bottom face to provide an attachment point for ligation material.

19. The dam clamp of claim 15 further comprising a radiographically opaque identification tab disposed in said bottom face.

20. The dam clamp of claim 15 wherein one or both faces of the clamp are composed of materials which are substantially transparent or translucent to visible light.

21. A dam clamp comprising two L-shaped plastic members joined together by a U-shaped bridge, said plastic members each having a side face and a bottom face, said side faces adapted to be bonded to a tooth via a bonding compound.

22. The dam clamp of claim 21 further comprising an aperture disposed through said side faces to aid in bonding the clamp to a tooth.

23. The dam clamp of claim 21 further including a radiographically opaque identification tab disposed in said bottom face.

24. A dam clamp comprising:
   a bottom surface and two side surfaces, said side surfaces joined to each other and to the bottom surface in such a fashion so as to allow the clamp to be secured in the interproximal area between two teeth, said side surfaces adapted to be bonded to a tooth via a bonding compound.

25. The dam clamp of claim 24 further including an aperture disposed in one or both side surfaces to aid in bonding the clamp to a given tooth.

26. The dam clamp of claim 24 further including an aperture disposed in said bottom surface to provide an attachment point for ligation material.

27. The dam clamp of claim 24 further including a radiographically opaque tab disposed in said bottom face.

* * * * *

UNITED STATES PATENT AND TRADEMARK OFFICE
CERTIFICATE OF CORRECTION

PATENT NO. : 4,773,857

DATED : September 27, 1988

INVENTOR(S) : HERMON K. HERRIN

It is certified that error appears in the above-identified patent and that said Letters Patent are hereby corrected as shown below:

In the Specification
    Column 3, line 36, "illustrate a perspective view" should read --illustrate perspective views--.

In the Claims
    Column 5, line 11, "ide" should read --side--.
    Column 5, line 46, "to attach a" should read --to attach to a--.

Signed and Sealed this

Twenty-first Day of February, 1989

Attest:

DONALD J. QUIGG

*Attesting Officer*     *Commissioner of Patents and Trademarks*